US005686078A

United States Patent [19]

[11] Patent Number: 5,686,078

[45] Date of Patent: Nov. 11, 1997

Becker et al.

[54] PRIMARY AND SECONDARY IMMUNIZATION WITH DIFFERENT PHYSIO-CHEMICAL FORMS OF ANTIGEN

[75] Inventors: Robert S. Becker, Henryville; Laura Ferguson, Bethlehem; Lorne Erdile, Stroudsberg; Maurice W. Harmon, Tannersville; Robert Huebner, Bartonsville, all of Pa.

[73] Assignee: Connaught Laboratories, Inc., Swiftwater, Pa.

[21] Appl. No.: 385,586

[22] Filed: Feb. 8, 1995

Related U.S. Application Data

[63] Continuation of Ser. No. 943,247, Sep. 14, 1992, abandoned.

[51] Int. Cl.$^6$ ........................ A61K 39/145; A61K 39/12; A61K 39/00; A61K 39/002

[52] U.S. Cl. .................................... 424/209.1; 424/208.1; 424/234.1; 424/265.1; 424/269.1

[58] Field of Search ............................. 424/209.1, 208.1, 424/204.1, 234.1, 265.1, 269.1

[56] References Cited

U.S. PATENT DOCUMENTS 4,496,538 1/1985 Gordon .................................... 424/92
4,619,828 10/1986 Gordon .................................... 424/92
4,950,480 8/1990 Barber et al. .......................... 424/85.8

OTHER PUBLICATIONS

Paul, Ed, Fundamental Immunol. (3rd Edition), 1993 Chapter 37, pp. 1312–1322. Attenuated Viral Vaccines.
McLaren, et al, 1980, "Comparative Antigenicity and Immunogenicity . . . " Infect. and Immunity vol. 28(1): 171–177.
Pharmaceutical Sciences, 1990, "Influenza Virus Vaccines" 1395–1397.
Butini, et al, 1994, "Comparative Analysis of HIV–Specific CTL . . . ". Abstract J306, J. Cell. Biochem Suppl. 18 B.
Haynes, 1993, "Scientific and Social Issues of Human . . . ". Science 260: 1279–1286.
Webster's Ninth New Collegiate Dictionary, 1990, p. 602.
Bulkovic, et al, 1987, "Immunoglobulin G Subclass . . . " Antiviral Research 8: 151–160.

*Primary Examiner*—Lynette F. Smith
*Attorney, Agent, or Firm*—Curtis, Morris & Safford P.C.

[57] ABSTRACT

Animals, including humans, are immunized by antigens, for example, the HA antigen of influenza, by first administering to a naive animal a normally strongly-immunogenic form of the antigen, for example, inactiviated or attenuated whole cell virus and subsequently administering a normally weakly-immunogenic isolated and purified viral antigen, to achieve an enhanced immune response to the purified viral antigen.

10 Claims, 3 Drawing Sheets

| GROUP | PRIMARY IMMUNIZATION | SECONDARY IMMUNIZATION |
|---|---|---|
| 1 | 1.0 μg HAp | 1.0 μg HAp |
| 2 | 1.0 μg WHOLE INACTIVATED VIRUS | 0.1 μg WHOLE INACTIVATED VIRUS |
| 3 | 1.0 μg WHOLE INACTIVATED VIRUS | 1.0 μg HAp + 0.1 μg WHOLE INACTIVATED VIRUS |
| 4 | 1.0 μg WHOLE INACTIVATED VIRUS | 1.0 μg HAp + 0.1 μg SPLIT HA |
| 5 | 1.0 μg WHOLE INACTIVATED VIRUS | 1.0 μg HAp |

| GROUPS | PRIMARY IMMUNIZATION | SECONDARY IMMUNIZATION |
|---|---|---|
| 1 | 1.0 mg HAp | 1.0 mg HAp |
| 2 | 0.1 mg SPLIT HA | 0.1 mg SPLIT HA |
| 3 | 1.0 mg HAp+0.1 mg SPLIT HA | 1.0 mg HAp+0.1 mg SPLIT HA |
| 4 | 1.0 mg SPLIT HA | 1.0 mg HAp+0.1 mg SPLIT HA |
| 5 | 1.0 mg SPLIT HA | 1.0 mg SPLIT HA |
| 6 | 1.0 mg SPLIT HA | 1.0 mg HAp |

PRIMARY AND SECONDARY IMMUNIZATION WITH DIFFERENT PHYSIO-CHEMICAL FORMS OF ANTIGEN

This application is a continuation of application Ser. No. 07/943,247, filed Sep. 14, 1992 now abandoned.

FIELD OF INVENTION

The present invention relates to a novel immunization procedure for eliciting an immune response in animals, including humans.

BACKGROUND TO THE INVENTION

Vaccination is a procedure whereby an immune response to antigen can be achieved to protect a host from infection. Some antigens elicit a strong immune response and some a weak response. Attempts have been made to enhance the immune response of weakly-immunogenic materials. The use of chemical adjuvants achieves such potentiation but generally such materials are toxic chemicals which cannot be used in humans.

Another procedure for achieving potentiation is to conjugate the weakly-immunogenic material to a strongly-immunogenic material and administer the conjugate in a vaccine. For example, a conjugate of the capsular polysaccharide of *Haemophilus influenzae* type b to diphtheria toxoid, as described in U.S. Pat. Nos. 4,496,538 and 4,619,828, or a conjugate of a weak antigen to a monoclonal antibody targeting antigen-presenting cells, as described in U.S. Pat. No. 4,950,480, may be employed.

SUMMARY OF INVENTION

In accordance with the present invention, there is provided a novel procedure of vaccination to elicit an enhanced immune response to a normally weakly-immunogenic form of an antigen in an animal, by administering the antigen to an animal primed with a highly-immunogenic form of the antigen.

The immunogenic form of the antigen is administered first to the naive animal to achieve a primary immune response to the antigen. The weakly-immunogenic form of the antigen, generally an isolated purified antigen provided from natural sources or synthetically, which does not provide a primary immune response in a naive animal, then is administered to the primed animal to achieve a booster immune response to the antigen. The term "weakly-immunogenic" as used herein refers both to no immune response and a low immune response.

The present invention is applicable to a wide range of antigens whose different physio-chemical forms produce different immune responses. Such antigens may comprise viral, bacterial, fungal, protozan and parasitic proteins.

GENERAL DESCRIPTION OF INVENTION

There exists isolated purified antigens which exhibit the antigenicity of the whole virus or other highly-immunogenic physio-chemical forms of the antigen but are either non-immunogenic or poorly immunogenic, i.e. they elicit no or only a small immune response, in naive animals, including humans, whereas the whole virus or other highly-immunogenic physio-chemical forms of the antigen elicits a strong immune response. An example of such an antigen is the haemagglutinin antigen (HA) from influenza virus. The purified form of the HA is bromelain-cleaved to remove the hydrophobic tail HA(p).

Since the antigen is in pure form, it has little or no tendency to produce any adverse side effects and hence is a desirable material to use for vaccination. The present invention enables such materials to be employed in the vaccination of animals, including humans, against disease, by effecting a secondary immunization of the animal using the purified antigen. The primary immunization of the animal is effected using a strong-immunogenic form of the antigen, usually the inactivated or attenuated whole cell virus in the case of viral antigens.

The isolated purified form of the antigen may be prepared by separation from the whole cell or may be prepared synthetically, such as by chemical synthesis or by recombinant techniques. Among the weakly-immunogenic viral antigens which may be used in the invention are the haemagglutinin antigen of influenza, and the gp120 protein of retroviruses, especially HIV; as well as other viral proteins isolated from viral membranes. Among the weakly-immunogenic bacterial antigens which may be used in the invention is the non-lipidated form of the outer surface protein A (OspA) of *B. burgdorferi.*

The invention is illustrated hereinafter with respect to the haemagglutinin antigen (HA) from influenza virus as the booster antigen but it will be apparent from the results given both for animal tests for the HA antigen that the invention has application to a wide range of antigens. Also presented below is data with respect to the immune response to the outer surface protein A (OspA of *B. burgdorferi*. Lipidated OspA is a strong immunogen while non-lipidated OspA is not. However, an immune response to the OspA-NL was observed when administered as a booster to animals primed with OspA-L. The results presented show the generality of the procedure.

EXAMPLES

Example 1

This Example illustrates the effect of administration of HA to animals.

Figure 1:
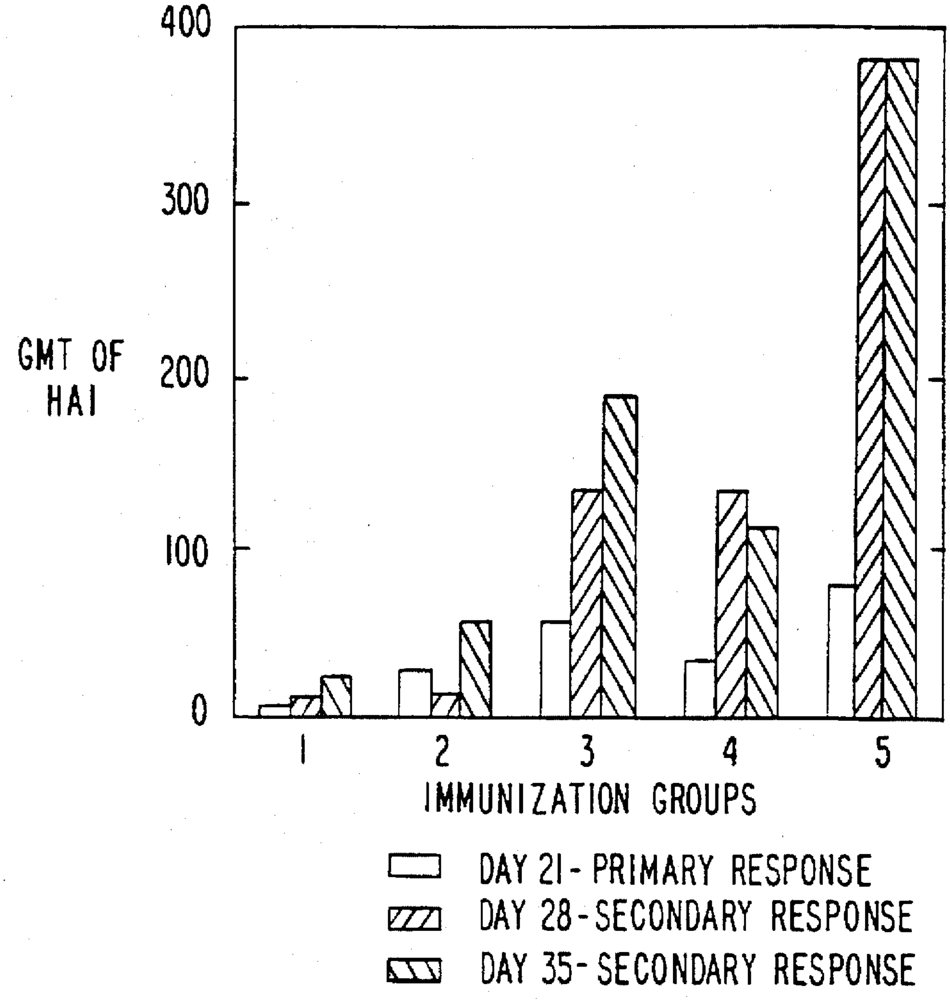
FIGS. 1 and 2 contain graphical data of HAI titers achieved by various forms of HA antigen in primed guinea pigs, as detail in Example 1 below.
Figure 2:
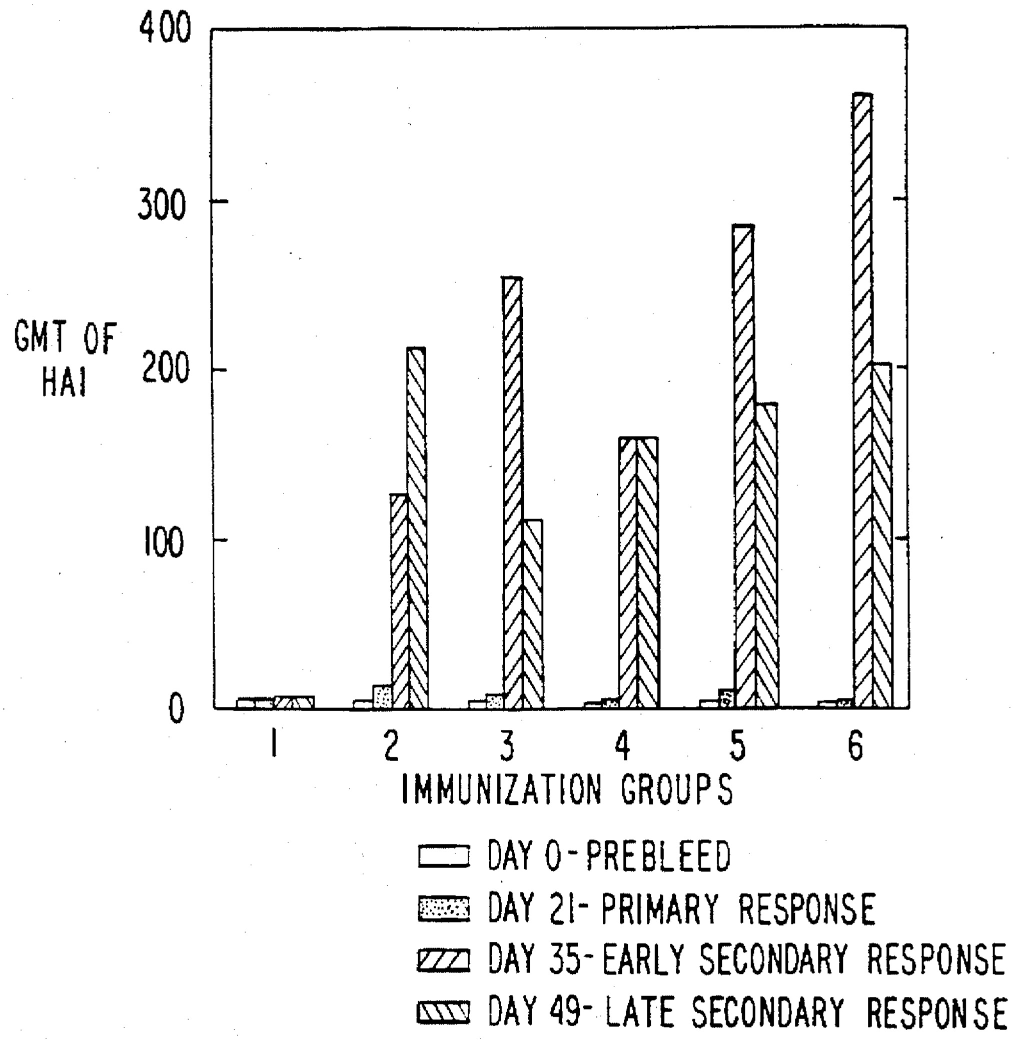

Guinea pigs were primed with either 1.0 μg of whole inactivated virus (results depicted in FIG. 1) or 1.0 μg of split HA i.e., FLUZONE®. (Split HA is provided by Triton X-100 detergent extraction of antigen from inactivated virus). The whole inactivated virus comprised an equal parts mixture of A/Taiwan and B/Panama formaldehyde inactivated influenza virus particles. The doses of whole inactivated virus refer to the dose of A/Taiwan material; (results depicted in FIG. 2). Three weeks later, the guinea pigs were given secondary immunization of either single flu antigen or coadministered flu antigens. The results shown in FIGS. 1 and 2 indicate that co-administration does not enhance anti-HA results in primed animals and hence the co-administration technique described in copending U.S. patent application Ser. No. 943,173 filed Sep. 14, 1992 by Becker et al and assigned to the assignee hereof, is useful only in naive animals if an enhanced immune response is to be achieved.

However, these results also show that the superior antigen for recalling memory responses was HA(p) alone, while immunization with HA(p) at the primary and secondary immunization did not generate a significant immune response. These results show that HA(p) can recall memory immune responses to the HA antigen but cannot itself generate memory. HA(p) is not immunogenic in naive animals or infants, even though it is antigenic in antibody-antigen reactions.

Example 2

The immunization procedure of Example 1 wherein various forms of HA or influenza infection were first administered to an animal followed by a booster administration was repeated in Swiss Webster mice. The results obtained are set forth in the following Table I:

TABLE I

Immunization of Normal and Previously Infected Mice with Flu Antigens

| Primary Immunization | Secondary Immunization | Dose (ng) | HAI Titer[2] 3 wk | HAI Titer 5 wk[4] | SN Titer 3 wk[4] | SN Titer[3] 5 wk |
|---|---|---|---|---|---|---|
| A/Taiwan Infection | Fluzone ® | 5 | 80 | 320 | 640 | 640 |
| A/Taiwan Infection | Fluzone ® | 50 | 40 | 640 | 80 | 2560 |
| A/Taiwan Infection | HA(p) | 450 | 80 | 1280 | 640 | 5120 |
| HA(p) | HA(p) | 450 | 5 | 5 | 5 | 5 |
| Fluzone ®[1] | Fluzone ® | 5 | 5 | 10 | 5 | 20 |
| Fluzone ®[1] | Fluzone ® | 50 | 10 | 40 | 5 | 80 |

[1]FLUZONE ® is a registered trademark of Connaught Laboratories, Inc. for a split HA influenza vaccine prepared from the A/Taiwan strain of influenza virus.
[2]HAI = haemagglutination inactivation
[3]SN = viral neutralization
[4]3 week sera = primary immune response; 5 week sera = secondary immune response These results also show the booster immune response to HA(p) in mice first immunized by whole inactivated virus.

Example 3

This Example illustrated the effect of administration of OspA in animals.

Figure 3:
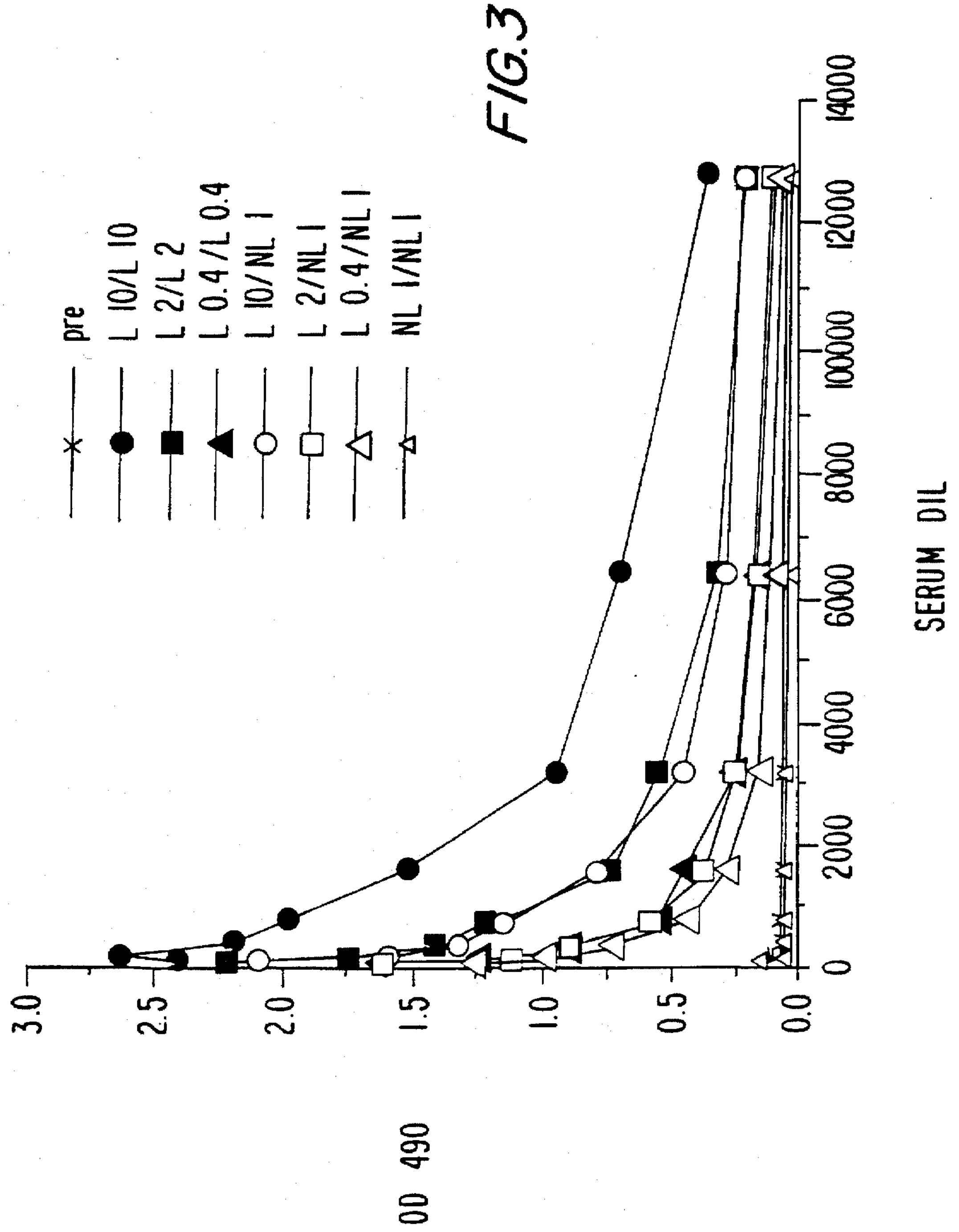
FIG. 3 contains graphical data of the immune response of various forms of OspA in mice.

The lipidated form of the OspA (OspA-L) protein of *B. burgdorferi* is a very potent immunogen in naive animals. Removal of the lipidated moiety from OspA (OspA-NL) dramatically decreases its immunogenicity in naive animals but not its antigenicity. OspA-L and OspA-NL were administered in varying amounts to C3H/He mice (Taconic Laboratories) in primary and secondary immunizations effected at days 0 and 21. The mice were bled at day 28. The dilution curves of an ELISA array of sera from the mice were plotted graphically and the results are seen in FIG. 3. It is apparent from the data that the booster administration of OspA-NL produced an immune response in mice given a primary administration of OspA-L.

SUMMARY OF DISCLOSURE

In summary of this disclosure, the present invention provides a novel immunization procedure which enables a strong immune response to be achieved from normally weakly-immunogenic purified viral proteins.

What we claim is:

1. A method of achieving an immune reaction to a highly-immunogenic form of a viral bacterial antigen in an animal, which consists essentially of the steps in the sequence set forth:

administering by vaccination to said animal the highly-immunogenic form of said antigen to achieve a primary immune reaction to the antigen, wherein the highly-immunogenic form of said antigen is particulate, and subsequently administering by vaccination to said animal a form of said antigen which is weakly-immunogenic and capable of recalling the memory immune reaction to the highly-immunogenic form of the antigen, to achieve a booster immune reaction to the antigen, wherein said weakly-immunogenic form of said antigen is soluble.

2. The method of claim 1 wherein said highly immunogenic form of the antigen is inactivated or attenuated whole cell virus.

3. The method of claim 2 wherein said weakly-immunogenic form of the antigen is an isolated and purified antigen.

4. The method of claim 3 wherein said antigen is isolated and purified from whole cells.

5. The method of claim 3 wherein said antigen is produced synthetically.

6. The method of claim 3 where said antigen is the HA(p) antigen from influenza virus.

7. The method of claim 3 wherein said antigen is the gp120 protein from HIV.

8. A method of claim 1 wherein the antigen is a bacterial antigen.

9. The method of claim 8 wherein said antigen is OspA-NL from *B. burgdorferi.*

10. The method of claim 1 wherein said animal is a human.

* * * * *

UNITED STATES PATENT AND TRADEMARK OFFICE
CERTIFICATE OF CORRECTION

PATENT NO. : 5,686,078

DATED : November 11, 1997

INVENTOR(S) : Becker et al.

It is certified that error appears in the above-indentified patent and that said Letters Patent is hereby corrected as shown below:

Claim 1, line 2: after "viral" please insert --or--.

Signed and Sealed this

Tenth Day of February, 1998

Attest:

BRUCE LEHMAN

*Attesting Officer* *Commissioner of Patents and Trademarks*